US008626953B2

(12) United States Patent  
Bucholz

(10) Patent No.: US 8,626,953 B2  
(45) Date of Patent: Jan. 7, 2014

(54) SYSTEM AND METHOD OF COMMUNICATING DATA FOR A HOSPITAL

(75) Inventor: Richard D. Bucholz, St. Louis, MO (US)

(73) Assignee: St. Louis University, St. Louis, MO (US)

( * ) Notice: Subject to any disclaimer, the term of this patent is extended or adjusted under 35 U.S.C. 154(b) by 1153 days.

(21) Appl. No.: 11/681,431

(22) Filed: Mar. 2, 2007

(65) Prior Publication Data

US 2007/0208833 A1    Sep. 6, 2007

Related U.S. Application Data

(60) Provisional application No. 60/778,664, filed on Mar. 3, 2006.

(51) Int. Cl.
*G05B 23/02* (2006.01)
*G06F 15/16* (2006.01)

(52) U.S. Cl.
USPC ............. 709/249; 709/208; 709/218; 340/3.1

(58) Field of Classification Search
USPC ............................ 709/249, 208, 218; 340/3.1
See application file for complete search history.

(56) References Cited

U.S. PATENT DOCUMENTS

| | | | |
|---|---|---|---|
| 4,644,582 A | 2/1987 | Morishita et al. |
| 4,722,056 A | 1/1988 | Roberts et al. |
| 4,815,106 A | 3/1989 | Propp et al. |
| 4,879,668 A | 11/1989 | Cline et al. |
| 4,958,283 A | 9/1990 | Tawara et al. |
| 4,987,412 A | 1/1991 | Vaitekunas et al. |
| 5,005,126 A | 4/1991 | Haskin |
| 5,027,422 A | 6/1991 | Peregrim et al. |
| 5,048,103 A | 9/1991 | Leclerc et al. |
| 5,051,720 A | 9/1991 | Kittirutsunetorn |
| 5,099,846 A | 3/1992 | Hardy |
| 5,241,472 A | 8/1993 | Gur et al. |
| 5,261,404 A | 11/1993 | Mick et al. |
| 5,272,625 A | 12/1993 | Nishihara et al. |

(Continued)

FOREIGN PATENT DOCUMENTS

| | | | |
|---|---|---|---|
| EP | 0833266 A2 | 4/1998 |
| EP | 0890919 A2 | 1/1999 |

(Continued)

OTHER PUBLICATIONS

Partial European Search Report, Application No. 07103539.8-1525, dated Sep. 5, 2008, 4 pages.

(Continued)

*Primary Examiner* — Rupal Dharia
*Assistant Examiner* — Joe Chacko
(74) *Attorney, Agent, or Firm* — Senniger Powers LLP

(57) ABSTRACT

A system used by a local health care facility to communicate with a remote health care facility via a data communication network. A controller at the local health care facility controls communication on the data communication network, including data communicated between the local health care facility and the remote health care facility. One or more devices located at the local health care facility transmit data to the remote health care facility via the data communication network. Additionally, the one or more devices receive control data via the data communication network and perform one or more functions in response to the received control data.

9 Claims, 4 Drawing Sheets

(56) References Cited

U.S. PATENT DOCUMENTS

| | | | |
|---|---|---|---|
| 5,274,551 | A | 12/1993 | Corby, Jr. |
| 5,284,142 | A | 2/1994 | Goble et al. |
| 5,291,401 | A * | 3/1994 | Robinson ............... 382/132 |
| 5,309,356 | A | 5/1994 | Nishide et al. |
| 5,353,220 | A | 10/1994 | Ito et al. |
| 5,383,454 | A | 1/1995 | Bucholz |
| 5,402,337 | A | 3/1995 | Nishide |
| 5,465,378 | A | 11/1995 | Duensing et al. |
| 5,483,606 | A | 1/1996 | Denber |
| 5,490,221 | A | 2/1996 | Ransford et al. |
| 5,531,227 | A | 7/1996 | Schneider |
| 5,531,520 | A | 7/1996 | Grimson et al. |
| 5,568,384 | A | 10/1996 | Robb et al. |
| 5,578,999 | A * | 11/1996 | Matsuzawa et al. ..... 340/825.22 |
| 5,581,638 | A | 12/1996 | Givens et al. |
| 5,615,112 | A | 3/1997 | Liu Sheng et al. |
| 5,631,844 | A | 5/1997 | Margrey et al. |
| 5,633,951 | A | 5/1997 | Moshfeghi |
| 5,659,792 | A | 8/1997 | Walmsley |
| 5,682,526 | A | 10/1997 | Smokoff et al. |
| 5,704,371 | A | 1/1998 | Shepard |
| 5,734,915 | A | 3/1998 | Roewer |
| 5,740,428 | A | 4/1998 | Mortimore et al. |
| 5,788,688 | A | 8/1998 | Bauer et al. |
| 5,819,229 | A | 10/1998 | Boppe |
| 5,826,102 | A | 10/1998 | Escobar et al. |
| 5,884,298 | A | 3/1999 | Smith, II et al. |
| 5,915,250 | A | 6/1999 | Jain et al. |
| 5,970,499 | A | 10/1999 | Smith et al. |
| 5,997,476 | A | 12/1999 | Brown |
| 5,997,528 | A | 12/1999 | Bisch et al. |
| 5,999,840 | A | 12/1999 | Grimson et al. |
| 6,003,007 | A | 12/1999 | DiRienzo |
| 6,073,101 | A * | 6/2000 | Maes ............................ 704/275 |
| 6,117,127 | A | 9/2000 | Helmreich et al. |
| 6,302,844 | B1 | 10/2001 | Walker et al. |
| 6,405,261 | B1 * | 6/2002 | Gaucher ....................... 709/250 |
| 6,466,971 | B1 | 10/2002 | Humpleman et al. |
| 6,661,784 | B1 | 12/2003 | Nykanen |
| 6,671,563 | B1 | 12/2003 | Engelson et al. |
| 6,783,523 | B2 | 8/2004 | Qin et al. |
| 6,928,490 | B1 | 8/2005 | Bucholz et al. |
| 2001/0037366 | A1 * | 11/2001 | Webb et al. .................. 709/204 |
| 2002/0118355 | A1 * | 8/2002 | Worthington et al. ......... 356/72 |
| 2003/0023459 | A1 | 1/2003 | Shipon |
| 2003/0233129 | A1 | 12/2003 | Matos |
| 2004/0158193 | A1 | 8/2004 | Bui et al. |
| 2005/0138186 | A1 * | 6/2005 | Hesselink et al. ............ 709/229 |

FOREIGN PATENT DOCUMENTS

| | | | | |
|---|---|---|---|---|
| WO | | 9424933 | A1 | 11/1994 |
| WO | | 9611624 | A2 | 4/1996 |
| WO | WO00/721180 | | * 11/2000 | ............... G06F 17/00 |

OTHER PUBLICATIONS

Jini, Distributed Event Specification—1.0, dated Jan. 25, 1999.
Jini, Architecture Specification—1.0, dated Jan. 25, 1999.
Jini, Lookup Service Specification—1.0, dated Jan. 25, 1999.
Jini, Device Architecture Specification—1.0, dated Jan. 25, 1999.
Christensen et al., "Individualizing Neuro-anatomical Atlases Using a Massively Parallel Computer," IEEE, Jan. 1996, pp. 32-38.
Rosenman et al., "Three-Dimensional Display Techniques in Radiation Therapy Treatment Planning," Int'l Radiation Oncology Biol., Phys., vol. 16, Jan. 1989, pp. 263-269.
Galvin, Jeffrey R., et al., "Imaging Corner, The Virtual Hospital, Providing Multimedia Decision Support Tools via the Internet," 1995, SPINE, vol. 20, No. 15, pp. 1735-1738.
Davis et al., "Three-Dimensional High-Resolution Volume Rendering (HRVR) of Computed Tomography Data: Applications to Otolaryngology—Head and Neck Surgery," Laryngoscope, vol. 101, Jun. 1991, pp. 573-582.
Rosenman et al., "Vistanet: Interactive Real-Time Calculation and Display of 3-Dimensional Radiation Dose: An Application of Gigabit Networking," Int'l J. Radiation Oncology Biol. Phys., vol. 25, Jan. 1993, pp. 123-129.
Heinz et al., "Examination of the Extracranial Carotid Bifurcation by Thin-Section Dynamic CT: Direct Visualization of Intimal Atheroma in Man (Part 1), " American Journal of Neuroradiology, Jul./Aug. 1984, pp. 355-359.
Hatch, "Reference-Display System for the Integration of CT Scanning and the Operating Microscope," Master of Engineering Thesis, Dartmouth College, Hanover, NH, Oct. 1984.
Pelizzari, Charles A., "Accurate Three Dimensional Registration of CT, PET, and/or MR Images of the Brain," J. of Computer Assisted Tomography, vol. 13, No. 1, pp. 20-26 (Jan.-Feb. 1989).
Gramkow, Claus, "Registration of 2D and 3D Medical Images,", Lyngby, IMMM-EKS-1996-1 (Jan. 1996).
Perry et al., "Emission and Transmission Spect Data Combination in Interactive 3D Image Presentation," The Journal of Nuclear Medicine, May 1989, p. 835, Abstract No. 443.
Tsui et al., "Three-Dimensional Display Methods for Image Data Obtained with Spect," European Journal of Nuclear Medicine, Aug. 1989, p. 558, Abstract No. 639.
Penn et al., "Stereotactic Surgery with Image Processing of Computerized Tomographic Scans,"Neurosurgery, vol. 3, No. 2, 1978, p. 157-163.
Rosenman et al., "Three-Dimensional Display Techniques in Radiation Therapy Treatment Planning," Int'l Radiation Oncology Biol., Phys., vol. 16, Jan. 1989, pp. 2635-2269.
Antonakopoulos, T., "A Spectrum Reuse/Token Passing (SRTP) Protocol for Communications in the Factory Environment Over the Power Grid," ISIE, Proceedings of the IEEE International Symposium on Industrial Electronics, Athens, Greece, Jul. 10-14, 1995, pp. 878-883, vol. 2, XP002172552, New York, New York.
PCT International Search Report Issued Application No. WO00/72180.

* cited by examiner

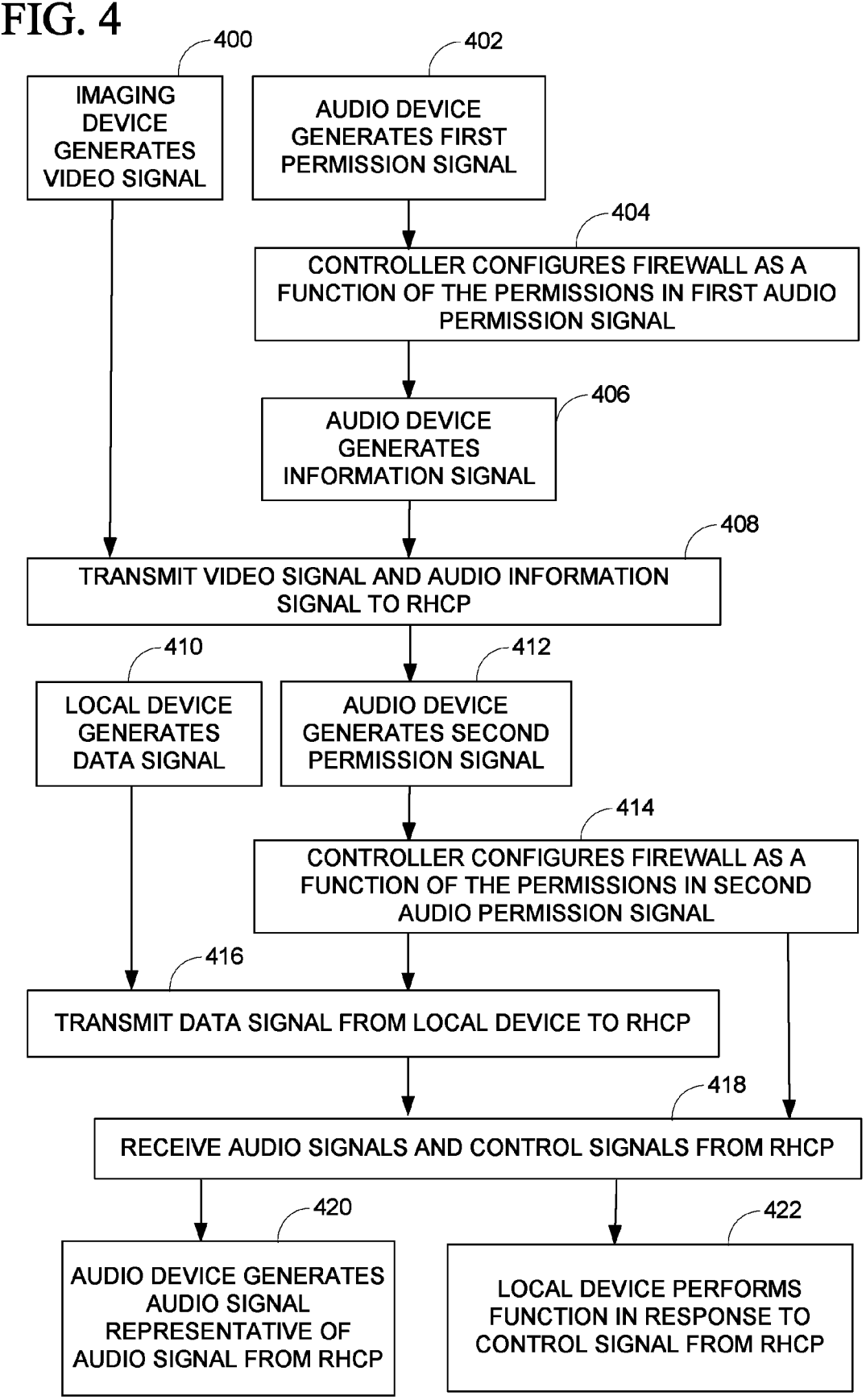

SYSTEM AND METHOD OF COMMUNICATING DATA FOR A HOSPITAL

CROSS-REFERENCE TO RELATED APPLICATION

This application claims the benefit of U.S. Provisional Application No. 60/778,664, filed Mar. 3, 2006, the entire disclosure of which is incorporated herein by reference.

BACKGROUND

Providing successful medical care is highly dependent on the skill of health care professionals in correctly selecting and performing medical procedures and the timeliness of performing the procedures. Currently, surgeons must perform increasingly complex procedures through progressively smaller openings in their patient's bodies while incurring the lowest possible incidence of complications and side effects. The exponential growth of medical knowledge and the rapid development and deployment of new therapeutic technologies intensify these demands. These developments constitute a constantly changing standard of care in the treatment of specific conditions from which the surgeon must rapidly choose the optimal care for a given patient during a surgical procedure. These decisions must be made within the financial context of a typical hospital experiencing tighter fiscal restraints and managed and staffed by employees experiencing rapid turnovers. In such a financial context, an experienced surgeon supported by experienced technicians is a rare combination. Yet, regardless of the staff and resource support, each patient expects optimal quality and results. Accordingly, surgeons are pressured to reduce the cost of their interventions and maximize the number of patients they see. As a result, some surgeons may have sufficient time to familiarize themselves with either complex surgical devices and the specific anatomy of the patient, and to keep up with every change in medical therapeutics as it occurs.

The challenge of providing successful medical care is further magnified in hospital emergency departments. Whereas most surgical interventions may be at least partially planned, interventions and interactions in the emergency department are completely dependent on the trauma that has occurred to the incoming patient. The emergency room (ER) care professionals may be confronted with a massive head injury, a simple laceration, a fractured bone, or massive internal bleeding. Although, ER care professionals are trained to triage these injuries to appropriate specialists, in certain situations, the appropriate specialists are not available. For instance, many rural hospitals are unable to staff a variety of specialists. Similarly, such a variety specialists are generally not present in battlefields. In these situations, the ER care professionals are unable to rely on a staffed specialist and must develop a complete diagnosis of the injuries received, and in many instances institute treatment. Where the injuries suffered by the patient are complex, the survival of the patient may ultimately hinge on a consultation with an expert specialist.

One prevalent cause of such complex injuries is motor vehicle crashes (MVCs). Particularly, MVCs are a major cause of traumatic brain injuries in persons ages 5-64 (Traumatic Brain Injury and Outcomes Associated with Motor Vehicle Crashes. University of Maryland CIREN Center. http://www-nrd.nhtsa.dot/gov/pdf/nrd-50/ciren/2004/1104Maryland.pdf). However, the majority of MVCs occur in rural areas and such rural crashes are generally more serve and result in greater injury than urban crashes (*Contrasting Rural and Urban Fatal Crashes* 1994-2003. NHTSA. December 2005. p I.). Thus, although expert specialists may be necessary for managing the complex injuries resulting from MVCs, the appropriate expert specialists may not be available for the majority of such injuries.

Even in situations where the assistance of expert specialists may be available, such assistance is untimely and thereby ineffective. Particularly, reliable assistance generally requires the ER care professional to contact and schedule a consultation with the appropriate specialist. In scheduling such a consultation, the ER care professional must attend to procedures required to uphold the patient's privacy rights. The delay resulting from properly acquiring of the assistance limits patient's recovery. For many complex trauma injuries, a short period of time, referred to as the "magic hour", exists after the injury where prompt resuscitation is critical to the patient's recovery, and in which secondary injuries, if allowed to occur, can be devastating to the patient's recovery. Thus, a need exists for a system and method which allows a local healthcare professional to promptly and securely communicate with a remote healthcare professional.

SUMMARY

Embodiments of the invention include a system and method of communicating data for use in a health care facility. In an embodiment, the invention provide a local health care professional (LHCP) located at a local health care facility with on-demand, instantaneous, and specialized health care assistance by a remote health care professional (RHCP) located at a remote health care facility via a data communication network. Additionally, embodiments of the invention allow the LHCP to control the data that is communicated via the data communication network.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other features will be in part apparent and in part pointed out hereinafter.

BRIEF DESCRIPTION OF THE DRAWINGS

FIG. 4 is a flow diagram illustrating selectively communicating data between a local health care professional at a local health care facility and a remote health care professional at a remote health care facility for providing the local health care professional with assistance from the remote health care professional, according to an embodiment of the invention.

Corresponding reference characters indicate corresponding parts throughout the drawings.

DETAILED DESCRIPTION

Embodiments of the invention provide a local health care professional (LHCP) located at a local health care facility with on-demand, instantaneous, and specialized health care assistance by a remote health care professional (RHCP) located at a remote health care facility. Particularly, embodiments of the present invention instantaneously link the LHCP to the RHCP in response to a verbal request for assistance. Embodiments of the invention further facilitate the need for timely and effective assistance by allowing the RHCP to remotely control local devices at the local health care facility using a control form modified for use by a RHCP. Additionally, embodiments contemplate the need to protect patients' privacy by restricting the recipient of data to a particular RHCP and restricting the content and source of the data communicated to the particular RHCP. Advantageously, embodiments of the present invention improve health care by providing secure and timely remote assistance to health care professionals.

Figure 1:
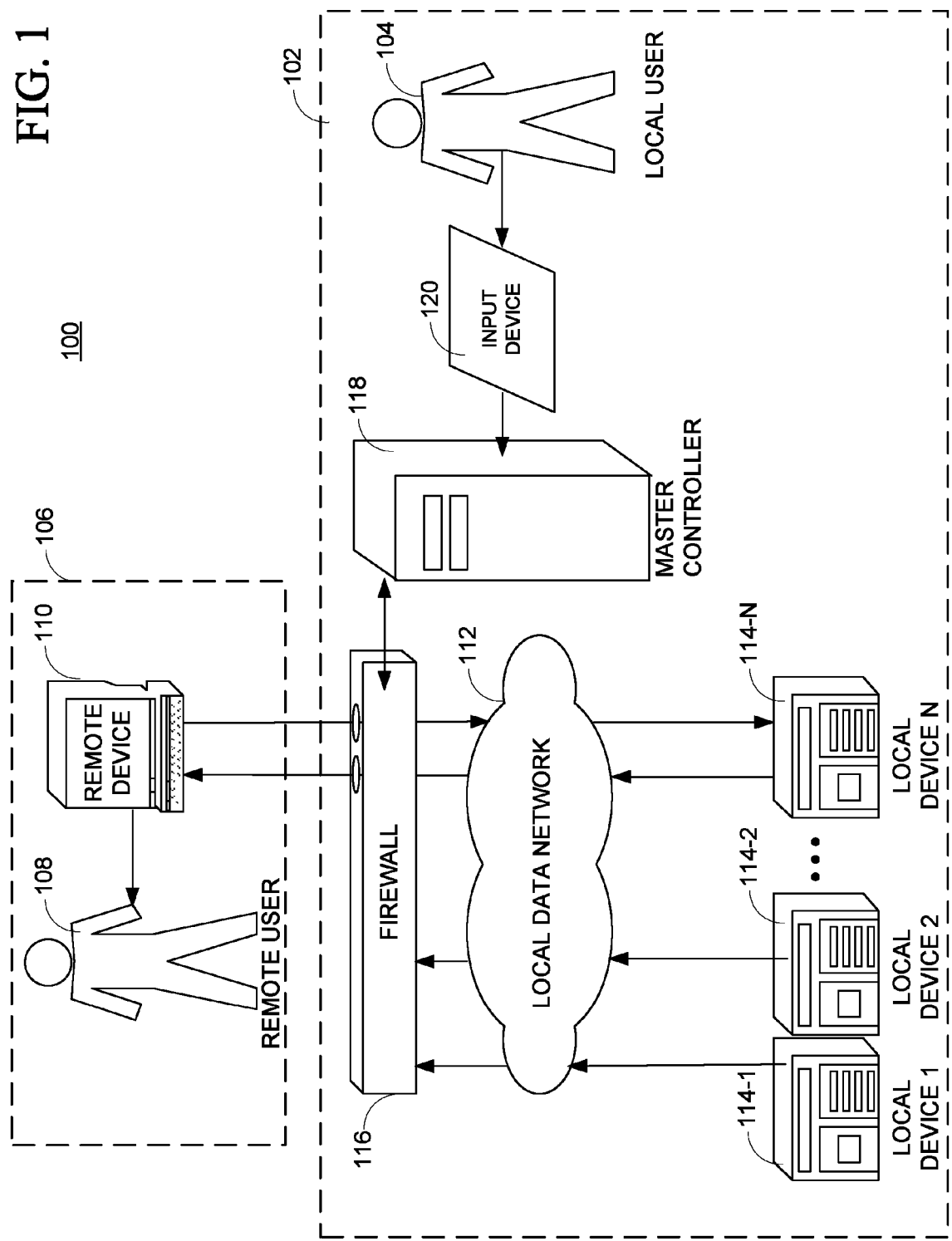
FIG. 1 is a block diagram illustrating a network environment for selectively communicating data between a local health care facility and a remote health care facility, according to an embodiment of the invention.

Referring first to FIG. 1, a block diagram illustrates an exemplary network environment 100 for use in a health care facility in which embodiments of the invention may be used to selectively communicate data. In general, the network environment 100 includes a local site 102 with a local user 104 and a remote site 106 with a remote user 108. According to embodiments of the invention, the local user is a LHCP 104 and the local site is a local health care facility 102. For example, the local user 104 may be a person who has experience and/or training as a paramedic, a medical technician, a nurse, a nurse's assistant, a physician's assistant, a physician, a veterinarian, or other administrator of health care. The local health care facility 102 may be any place where the LHCP 104 administers health care. Exemplary health care facilities include a hospital, a doctor's office, a private residence where a patient is being cared for, an ambulance or helicopter, a first aid station, a battalion aid station, and/or a mobile station. In the illustrated network environment 100, the remote user is a RHCP 108 and the remote site is a remote health care facility 106 which may include any location where the RHCP 108 administers health care assistance. For example, the remote site 106 may the RHCP's car when the RHCP 108 provides assistance via a cellular phone, PDA, or other mobile device. In another example, the remote health care facility 106 is a hospital or doctor's office.

While the remote health care facility 106 is located remote from the local health care facility 102, the local and remote health care facilities 102, 106 are connected such that the LHCP 104 is able to obtain assistance from the RHCP 108 by selectively communicating data between the two facilities, 102, 106. According to embodiments of the invention, the local health care facility 102 and the remote health care facility 106 are not limited to a physical location. For example, the local health care facility 102 may be a mobile aid station and the remote health care facility 106 may be the RHCP's medical office in the morning and the RHCP's personal home in the evening. Additionally, the local health care facility 102 and the remote health care facility 106 may be associated with the same entity or different entities. For example, the local health care facility 102 may be a public hospital building in Missouri and the remote health care facility 106 may be a private hospital building in Texas. In another example, the local health care facility 102 may be a hospital building on particular college campus and the remote health care facility 106 is a mile way at a doctor's office affiliated with the college.

In the network environment 100 illustrated in FIG. 1, the remote health care facility 106 includes a remote device 110 for receiving data from the local health care facility 102 and transmitting data to the local health care facility 102. In one embodiment, the remote device 110 is a computing device. Exemplary remote computing devices 110 include one or a combination of the following: a personal computer (PC), a workstation, a cellular phone, a portable digital device, a personal digital assistance (PDA), a pocket PC, a digital media player, and any other digital devices known in the art for remotely communicating data. As generally known to those skilled in the art, a computing device includes a combination of the following (not shown): a processing unit, a storage memory, an input device(s) (e.g., keyboard, mouse, trackball, pen, touch pad, microphone, joystick, gamepad, push button, touch screen, and other input devices known in the art), an output device(s) (e.g., monitor, printer, speakers, lights and other output devices known in the art), a networking device, other devices, and an internal bus system coupling to these components for connecting these components within the computing device.

According to the network environment 100 illustrated in FIG. 1, the local health care facility 102 includes a local data communication network 112 in communication with the remote device 110 at the remote health care facility 106 such that the LHCP 104 and the RHCP 108 can communicate with each other through devices located at their respective remote locations. According to embodiments of the invention, the local data communication network 112 may include a local area network (LAN), a wide area network (WAN), metropolitan/municipal network (MAN), a hospital or campus area network (CAN), and/or other area networks known in the art. The remote device 110 may be directly coupled to the to the local data communication network 112 or may be coupled to another data communication network (e.g., WAN such as the Internet) which is coupled to the local data communication network 112.

In the network environment 100 illustrated, the local health care facility 102 further includes one or more local devices 114 which are connected to the local data communication network 112. In one embodiment, the local devices 114 include a controllable component for performing one or more end functions and a controller connected to the controllable component for controlling the controllable component. The controllable component responds exclusively to signals transmitted from the controller. The controller is connected to the local data communication network 112 via a wired (e.g., wired network or direct-wired connection) or wireless (e.g., acoustic, radio frequency (RF), infrared) connection for transmitting data and/or receiving control signals/data via the local data communication network 112. In one embodiment, the local device 114 may be remotely controlled (e.g., perform specific functions) by control data transmitted via the local data communication network 112 to the controller of the local device 114. The control signals/data received by the controller via the local data communication network 112 influences the signals used by the controller to control the controllable component. Thus, the local device 114 is responsive to the control signal provided via the local data communication network 112. Exemplary local devices include a CT or MRI scanner, a hospital image retrieval system, hospital electronic health records (EHR), a digital stethoscope, an ultrasound device, a device for monitoring patient vital signs, a microscope, a bipolar coagulator, a camera, or any other device instrumental in administering health care.

In one embodiment, the local device 114 includes a memory (e.g., ROM) for storing a control form. The local device 114 may also include a display for displaying the user interface and a user interface for allowing a user to interact with the control form and obtaining control data associated with the user interactions. In particular, the control form associates a particular user input with a particular control signal used by the controller to control the controllable component. For example, an MRI scanner local device has a control form which uses html language to create virtual buttons (e.g., power, scan, zoom) which are displayed via a user interface on a touch screen to allow a user to control the MRI scanner local device. In one embodiment, the control form associated with the local device 114 is used by the LHCP 104 to control the local device. In another embodiment, the control form associated with the local device 114 is additionally or alternatively communicated to the remote device 110 to allow the remote device 110 to remotely control the local device 114 via the control form. In yet another embodiment, described below, the remote device 110 controls the local device 114 using a different control form which is based on the control form associated with the local device 114.

The local health care facility 102 further includes a firewall 116 associated with the local data communication network 112 and a master controller 118 for controlling the communication of data. The firewall 116 includes a set of parameters to control communication via the local data communication network 112 with devices located at the local health care facility 102 (e.g., local devices). The master controller 118 controls the firewall 116 to selectively link one or more device(s) located at the health care facility to the remote device 110 via the local data communication network 112 and selectively permits the device(s) to transmit data signals via the link and receive control signals via the link. For instance, the master controller 118 may control the firewall 116 parameters to allow local device N (114-N) to transmit data signals to and receive control signals from the remote device 110 via the local data communication network 112 while restricting local devices 1 and 2 (114-1, 114-2) from communicating via the local data communication network 112. In one embodiment, the firewall 116 is a software program residing on the master controller 118. In another embodiment, a device separate from the master controller 118 includes the firewall 116 and the master controller 118 is connected to the device which includes the firewall 116. For example, the firewall 116 is a hardware device or a portion of a hardware device which is connected to the local data communication network 112 and the master controller 118 is also connected to the local data communication network 112 such that the master controller 118 can control the firewall 116. In another example, the firewall 116 is a software program or application residing on a hardware device which is connected to the local data communication network 112 and the master controller 118 is also connected to the local data communication network 112 such that the master controller 118 can control the firewall 116.

The local health care facility 102 further includes an input device 120 connected to the master controller 118 via a wire (e.g., USB) or wireless (e.g., acoustic, radio frequency (RF), infrared) connection for providing a control interface to the LHCP 104. The input device 120 obtains an input from the LHCP 104 and transmits a data signal representative of the input from the LHCP 104. In one embodiment, the input indicates a particular parameter of the firewall 116. In another embodiment, the input additionally or alternatively includes data for communicating to the remote health care facility 106. Exemplary input devices 120 include a keyboard, a mouse, a switch, a microphone, or a joystick. In one embodiment, the input device 120 includes an output component for receiving a signal from the master controller 118 and delivering data representative of the received signal to the LHCP 104. Exemplary input devices 120 including an output component include a phone, an audio device 204, a personal digital assistant (PDA), or a touch screen.

Figure 2:
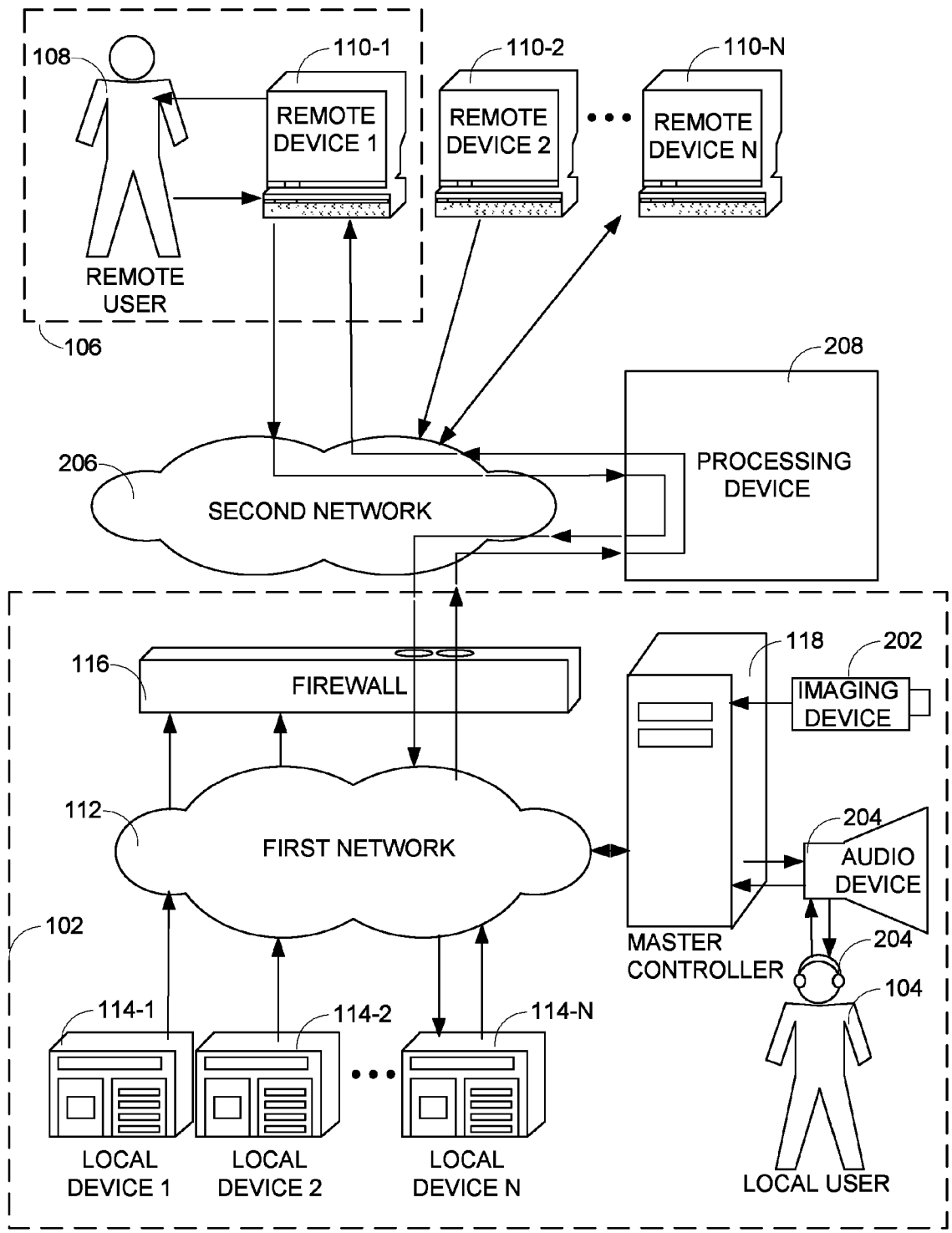
FIG. 2 is an exemplary block diagram illustrating an exemplary system for use in a health care facility to provide a local health care professional at a local health care facility with assistance from a remote health care professional at a remote health care facility in response to a verbal request from the local health care professional, according to an embodiment of the invention.

In an embodiment illustrated in FIG. 2, an exemplary system employing the network environment 100 is used to provide the LHCP 104 with on-demand, instantaneous, and specialized health care assistance by the RHCP 108 at the remote health care facility 106. The LHCP 104 is equipped with the master controller 118 for initiating assistance and controlling communication via a first network 112 (e.g., local area network). In one embodiment, the master controller 118 is a small computing device that is affixed to the body of the LCHP, minimizing cables which clutter health care facility rooms. For example, the master controller 118 is attached to a belt worn by the LHCP 104 and operates under battery power. In this example, the belt may include slots securing extra charged batteries. In one embodiment, the master controller 118 runs software programs (e.g., voice recognition) to interface with input devices 120 and/or output devices connected to the master controller 118. In one embodiment, the master controller 118 includes a removable memory device for storing data associated with the LHCP 104. For example, the master controller 118 includes a secure digital card which has preferences (e.g., preferences for control forms for controlling local devices) and speech files associated with the LHCP 104.

An imaging device 120 located at the local health care facility 102 is wire (e.g., USB) or wirelessly (e.g., acoustic, radio frequency (RF), infrared) coupled to the master controller 118 for generating a video signal representative of images at the local health care facility 102. The master controller 118 receives the video signal from the imaging device 120 and adapts it (e.g., using MPEG-4) for sending to the RHCP 108. In one embodiment, the imaging device 120 is affixed to the LHCP 104. In another embodiment, the imaging device 120 further includes a light. For example, a camera with an integrated light is attached to protective eyewear worn by the LHCP 104 and is connected by a cable to the master controller 118 attached to the belt worn by the LHCP 104. Advantageously, the LHCP 104 does not have to hold the camera and the light enhances the visibility of dark areas and serves as a guide allowing the LHCP 104 to aim the camera at a particular area (e.g., a body cavity of a patient undergoing surgery).

An input device 120, such as an audio device 204, located at the local health care facility 102 is wire or wirelessly coupled to the master controller 118 for generating audio signals representative of a sound patterns verbally created by the LHCP 104. The master controller 118 receives the audio signals from the imaging device 120. In one embodiment, the master controller 118 recognizes the audio signal as a particular verbal request by the LHCP 104 and responds to the request. Requests made by the LHCP 104 may include initiating communication with a remote device 110/RHCP 108, permitting transmission of data signals from devices located at the local health care facility 102, and permitting the receipt by devices located at the local health care facility 102 of data signals and/or control signals transmitted from devices located remote to the local health care facility 102, and permitting the receipt and/or transmission between devices located at the local facility. For example, the LHCP 104 says "initiate communication with Dr. Jones", the audio device 204 generates an audio signal representative of the request, the master controller 118 recognizes the audio signal (e.g., using voice recognition software running on the master controller 118 and speech files stored on a memory card read by the master controller 118) as a request to communicate with Dr. Jones and responds to the request by linking a remote device 110 associated with Dr. Jones to the master controller 118. In another embodiment, the master controller 118 additionally or alternatively adapts the audio signal for sending to the RHCP 108. For example, the LHCP 104 says "the patient was in a car accident approximately 20 minutes ago and has been unconscious for the last 7 minutes," the audio device 204 generates an audio signal representative of the information, and the master controller 118 adapts the audio signal (e.g., using MPEG-4) for sending to the remote device 110 of the RHCP 108 (e.g., Dr. Jones). In one embodiment, the audio device 204 also includes an output component for generating a sound pattern from an audio signal received from the master controller 118. For example, an audio signal representative of the RHCP's verbal instructions is transmitted via the first data network 112 to the master controller 118 and is in turn received by the audio device 204. The audio device 204 generates a sound pattern which can be heard by the LHCP 104. Thus, the LHCP 104 and the RHCP 108 can communicate verbally. In the illustrated embodiment, the audio device 204 is affixed to the LHCP 104. For example, the audio device 204 is a headset worn by the LHCP 104 and is connected by a cable to the master controller 118 attached to the belt worn by the LHCP 104.

The master controller 118 having the audio device 204 and the imaging device 120 coupled thereto is connected wire or wirelessly to the first network 112 (e.g., local area network) located at the local health care facility 102. The first network 112 is associated with a programmable firewall 116 controlling communication on the first network 112. In the illustrated embodiment, the master controller 118 controls the firewall 116 as a function of the audio signal received by the audio device 204. For example, the LHCP 104 says "transmit video signal to remote device 110", the audio device 204 generates an audio signal representative of the request, and the master controller 118 receives and recognizes the request. The master controller 118 then transmits to the firewall 116 a signal to program the firewall 116 so as to permit the video signal from the imaging device 120 to transmit video signals to the remote device 110. The firewall 116 also controls communication (e.g., transmission of data signals and receiving of control signals) of local devices 114 at the local health care facility 102 which are connected wire or wirelessly to the first network 112. In one embodiment, the master controller 118 specifies particular content permitted for sending in the data signal to the RHCP 108 via the first network 112. For example, the LCHP says "transmit electronic hospital records for current patient," the master controller 118 accordingly controls the firewall 116 to allow the transmission of only those hospital records for the current patient, and the local device which includes electronic hospital records transmits a data signal to the RHCP 108 which includes the hospital records for the current patient only. Advantageously, the LHCP 104 is able to quickly communicate vital information with the RHCP 108 while protecting patient privacy by preventing the RHCP 108 from accessing other patient records and sharing the current patient information exclusively with the RHCP 108.

In the embodiment illustrated in FIG. 2, a plurality of remote devices 110 located at one or more remote health care facilities 106 is connected to a second network 206 (e.g., the Internet) which is connected to the first network 112 (e.g., local health care facility 102 trauma bay intranet). Each of the remote device 110s are associated with providing a particular assistance to the LHCP 104. For example, a first remote device 110-1 is a PDA of a cardiologist for providing remote cardiology assistance, a second remote device 110-2 is a computing device located in the neurosurgery department of hospital in Kansas for providing remote assistance with neurosurgery, and a third remote device 110-3 is a computing device located in the pediatric surgery department of a hospital in Missouri for providing assistance with pediatric patients. A processing device 208 is coupled to the remote device 110s and the devices at the local health care facility 102 for locating the appropriate remote device 110 based on a communication request from the LHCP 104. The processing device 208 is coupled to the plurality remote devices 110 via the second network 206 and to the master controller 118 and the local devices via the first network 112. For example, the processing device 208 may be a server having a website associated therewith and the first, second, and third remote devices 110-1, 110-2, 110-3, and the master controller 118, and the local devices 114 are connected to the website. In the illustrated embodiment, the master controller 118 sends data to the processing device 208 via the first network 112 to initiate remote communication. The data indicates one or more devices located at the local health care facility 102 (e.g., the imaging device 120, the audio device 204, the local devices) selected by the LHCP 104 via the master controller 118 for linking to a remote device 110. The processing device 208 locates the appropriate remote device 110 based on the data, and the remote device 110 is then linked to the selected device(s) for communicating in accordance with the firewall 116.

In one embodiment, the data sent to the processing device 208 for initiating communication identifies a specific remote device 110 (e.g., IP address, or hospital+RHCP's name). In another embodiment, the data sent identifies one or more medical credentials of a RHCP 108 (e.g., neurosurgeon) and the processing device 208 locates the second remote device 110-2 (e.g., the computing device associated with neurosurgery department) where the second remote device 110-2 is available and connected to the processing device 208 (e.g., logged into the website). In yet another embodiment, the data includes a general request for remote communication and additional data which responds to the processing device 208 prompting the master controller 118 for additional data needed to locate the particular remote device 110. For example, the LHCP 104 says "initiate communication" and the master controller 118 sends a corresponding data signal (e.g., a first collection of data) to the processing device 208 for requesting communication with a remote device. The processing device 208 receives the data and then prompts the master controller 118 for additional data needed to locate/identify a particular remote device 110. For instance, the processing device 208 may include an automated audio system or a live receptionist that receives the request and responds by sending the master controller 118 an audio signal asking the type of injury suffered by the patient. The master controller 118 transmits a data signal (e.g., second collection of data) responding to the inquiry in accordance with the LHCP's verbal response (e.g., "heart attack") via the audio device 204.

Figure 3A:
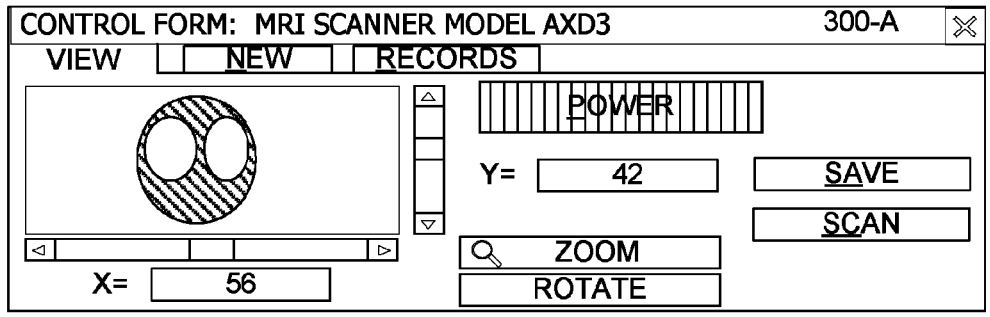
FIGS. 3A and 3B are drawings of screen shots illustrating primary control forms associated with local devices, according to an embodiment of the invention.
Figure 3B:
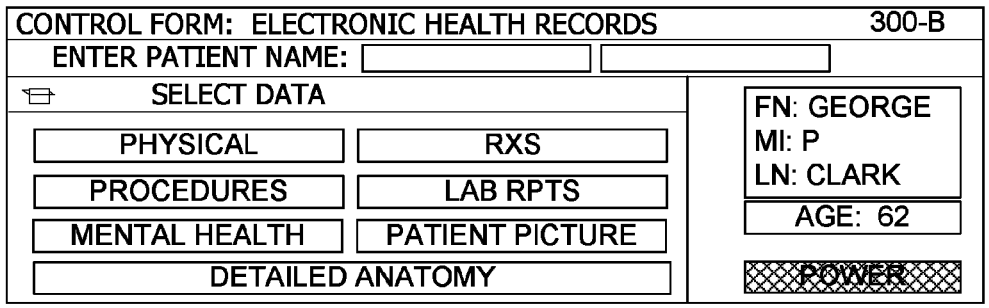
Figure 3C:
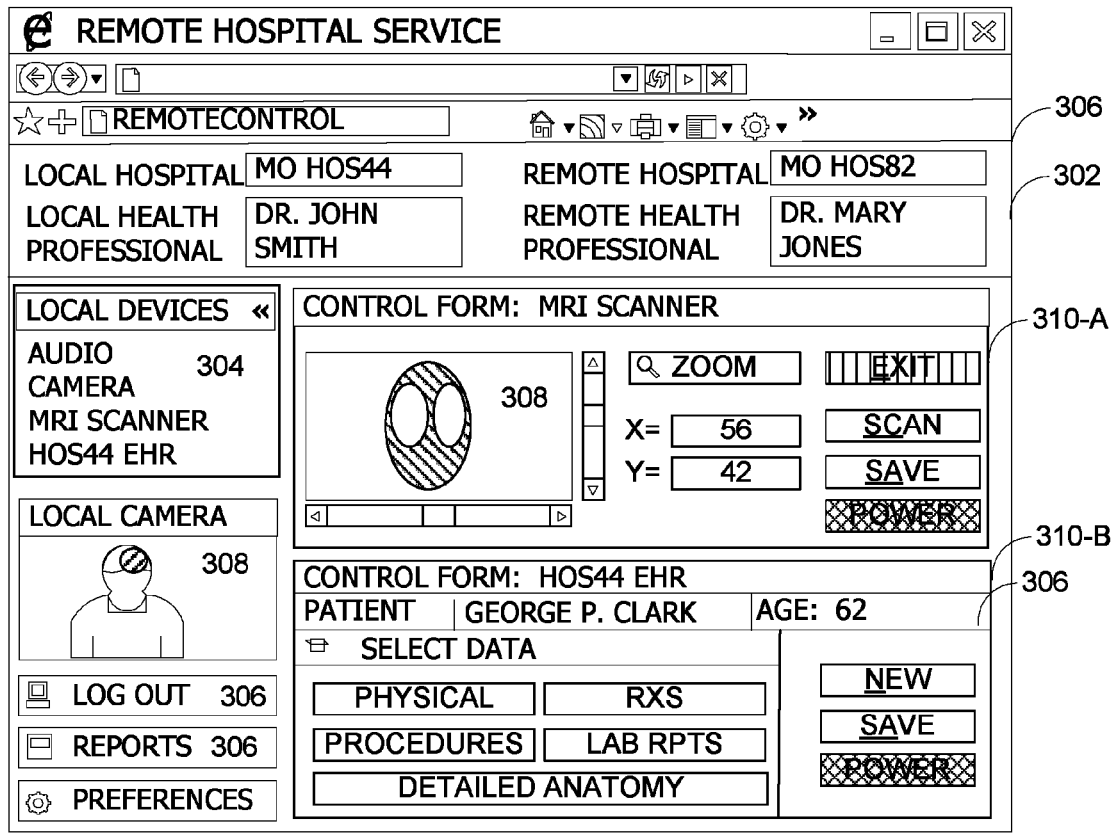
FIG. 3C is a drawing of a screen shot illustrating modified control forms associated with local devices located at a local health care facility modified for providing to a remote health care professional via a remote device located at a remote health care facility, according to an embodiment of the invention.

Referring to FIG. 3C, an exemplary screen shot 300 of a webpage of the website associated with the processing device 208, according to one embodiment of the invention. In the illustrated screen shot, the web page processed by the processing device 208 includes information identifying the parties involved in the communication 302, information for identifying the devices at the local site involved in the communication 304, navigation controls 306 for accessing other web pages associated with the web site, display features 308 for simultaneously displaying data streams (e.g., audio, video, text, image) transmitted from device(s), and control forms 310 associated with local devices 114 for remotely controlling the devices. Thus, the processing device 208 simultaneously receives the video stream from the imaging device 120 and the MRI Scanner, text data from the MRI Scanner and the EHR device, and audio streams (not shown) from the audio device 204. Concurrent with the receiving of multiple data streams, the processing device 208 additionally transmits multiple streams of data to the devices located at the local hospital facility. Advantageously, the processing device 208 simultaneously processes multiple bidirectional data streams associated with multiple devices and displays the processed data on a single user-friendly web page allowing the RHCP 108 to provide efficient assistance.

According to the illustrated embodiment, LHCP 104, Dr. John Smith 302 at local health care facility, MO HOS44 304, has requested remote communication. For example, Dr. John Smith has verbally requested communication and the master controller 118 has transmitted a signal to the processing device 208 requesting communication and identifying Dr. John Smith as the LHCP 104 and MO HOS44 as the local health care facility 102. The master controller 118 has provided the processing device 208 with data for locating a remote device 110 associated with RHCP 108, Dr. Mary Jones 306, at remote health care facility 106 MO HOS82 308. Additionally, the master controller 118 has controlled the firewall 116 associated with the network at MO HOS44 in order selectively link devices at the local health care facility 102 (the local camera, the MRI Scanner, and the Electronic Hospital Records Device (HOS44 EHR)) to the remote device 110. The processing device 208 processes data communicated from the local health care facility 102 and includes content from the data on the web page. A display and a user interface (e.g., web browser) associated with the remote device 110 displays the web page 300 and allows the user to interact with the web page. The processing device 208 processes signals transmitted from the remote device 110 to the processing device 208 indicating the user's interactions with the web page.

In the screenshot illustrated in FIG. 3C, the web page includes displayed control forms 310 associated with local devices selectively linked to the remote device 110. In one embodiment, the processing device 208 includes a memory and stores a primary control form and data associating the control form with the local device. In another embodiment, the local device 114 stores the primary control form and transmits the control form to the processing device 208 when the local device 114 is linked to the remote device 110. Accordingly, the processing device 208 configures the web page based on the stored or received control forms. In one embodiment, the processing device 208 may modify the primary control form and include the modified control form on the webpage. The modification may be based on data stored by the processing device 208, data received from the local health care facility 102 via the first and second networks, and/or data received from the remote health care facility 106 via the second network.

Referring to FIGS. 3A, 3B and 3C, in one embodiment, the processing device 208 displays a control form 310-A, 310-B (e.g., graphic user interface). The displayed control forms 310-A, 310-B are generated by modifying the primary control forms 300-A, 300-B based on the identity of the RHCP 108. According to the embodiment illustrated by FIGS. 3A and 3C, the processing device 208 modifies the primary control form 300-A, 300-B based on preferences associated with the RHCP 108. The processing device 208 stores preferences associated with identifying information associated with the RHCP 108 (e.g., a login ID). When the RHCP 108 logins to provide remote assistance, the processing device 208 modifies the control forms of local devices according to the preferences. The primary control form for the MRI scanner 300-A illustrated in FIG. 3A locates the X and Y coordinates on the X and Y axis of the associated image, the zoom button at the top of the control form, and the rotate button at the bottom of the control form. The RHCP 108 has preferences indicating a different location for the X and Y axis and to hide the rotate button as shown in the displayed control form 310-A of FIG. 3C. According to the embodiment illustrated by FIGS. 3B and 3C, the processing may additionally or alternatively modify the primary control form 300 based on an access level associated with the RHCP 108. The access level could be based on a number of factors such as the relationship between the patient and the doctor (e.g., whether the doctor is the primary doctor), the type of RHCP 108 (e.g., technicians restricted to particular controls), the relevancy of the information, whether patient has signed a release for the information). The primary control form associated with the EHR 300-B illustrated in FIG. 3B includes buttons for accessing mental health records and a picture of the selected patient. These buttons are eliminated from the control form 310-B displayed in FIG. 3C because Dr. Mary Jones is not associated with access to the buttons.

In one embodiment, the processing device 208 displays a control form 310 which additionally or alternatively modifies the primary control form 300 in order to standardize the control form. Particularly, the primary control form 300 is modified to standardize at least one feature associated with a function performed by local devices 114 located at a plurality of remote health care facilities 108 so that the standardized feature appears substantially similar in the control forms 310 displayed for each of the local devices 114. In one example, for all devices having an on/off function, the "power" button associated with the on/off function is shaded and located at the lower right hand side of the control form 310-A, 310-B. In another example, all devices of a particular type, such as all MRI scanning devices (regardless of the model number) display the image on the left side of the control form 310-A and use scroll bars adjust the image (e.g., rather than buttons, touching on the edge of the image, dragging the edge of the image). Advantageously, standardizing features of the control form eliminates the time required for the RHCP 108 to become familiar with the particular controls of a particular local device 114.

The flow diagram of FIG. 4 illustrates operations for selectively communicating between a LHCP 104 at a local health care facility 102 and a RHCP 108 at a remote health care facility 106 via a data communication network (e.g., 112 and 206) according to an embodiment of the invention. In one embodiment, the data communication network includes a network 112 associated with the local health care facility 102 and controlled by a firewall 116. At 400, the imaging device 120 generates a video signal (e.g., video of injured portion of patient). In one embodiment the imaging device 120 is a camera coupled to a controller 118 and the controller 118 is connected to the data communication network. At 402, the audio device 204 generates a first permission signal. In one embodiment, the audio signal is representative of a request verbalized by the LHCP 104 (e.g., "permit transmission of imaging signal from imaging device 120 and audio communication with the audio device 204"). The request permits transmitting of the video signal generated by the imaging device 120 via the data communication network to the RHCP 108 and permits transmitting to and receiving from the RHCP 108 audio signal via the data communication network.

The audio signal is received by the controller 118 and the controller 118 recognizes the communication request. In one embodiment, the controller 118 has voice recognition software and speech files associated with the LHCP 104 which are used to recognize the communication request. At 404, the controller 118 configures the firewall 116 associated with data communication network as a function of the permissions included in the first audio signal. Thus, the controller 118 configures the firewall 116 to allow the transmission of the video signal to the RHCP 108 and to allow bidirectional communication of audio signals between the RHCP 108 and the audio device 204.

At 406, the audio device 204 audio device 204 generates audio signals including information verbalized by the LHCP 104 for to communicating to the RHCP 108 (e.g., status of the patient, information regarding the patient's injuries, questions regarding patient diagnosis/treatment). The controller 118 receives the audio signals including the information and determines the signal is not a communication request. The controller 118 then converts the audio signal to be transmitted via the data communication network. The controller 118 similarly receives the video signal generated by the imaging device 120 and converts the video signal to be transmitted via the data communication network. At 408, the controller 118 transmits the converted video and audio information signals to a remote device 110 associated with the RHCP 108. In one embodiment, a processing device 208 connected to the data communication network, such as a server associated with a website/web pages, is used to locate an appropriate remote device 110 and a particular RHCP 108. The appropriate remote device 110 then accesses the video signals through a web page via the data communication network.

At 410, one or more local devices located at the local health care facility 102 generate data signals. For example, a heart monitor obtains data regarding the functioning of the patient's heart and an MRI scanner is initialized and generates a data signal indicating a "ready" status. At 412, the audio device 204 generates a second permission signal. In one embodiment, the second permission signal is representative of a second communication request verbalized by the LHCP 104. For example, the second communication request permits one or more local devices located at the local health care facility 102 and coupled to the data communication network to transmit data signals to the remote device 110 and receive control signals from the remote device 110 via the data communication network. In another example, the second communication request specifies the particular content of the data permitted to be included in the data signals (e.g., restrictions based on a particular patient, a particular injury received by a particular patient, information obtained during a certain time period regarding a particular patient, information obtained from a particular source regarding a particular patient) transmitted by the local device(s). Similarly, the second communication request may also specify the particular content permitted to be included in the control signals (e.g., restrictions based on functions the LCHP designates to be remote controlled, restrictions based on the identity of the RHCP 108) received by the local device(s).

The second audio permission signal is received by the controller 118 and the controller 118 recognizes the communication request. In one embodiment, the controller 118 has voice recognition software and speech files associated with the LHCP 104 which are used to recognize the second communication request. At 414, the controller 118 configures the firewall 116 associated with data communication network as a function of the permissions included in the second audio permission signal. Thus, the controller 118 configures the firewall 116 to allow the transmission of the data signal(s) to the remote device 110 and to allow the local device(s) to receive control signal(s) via the data communication network from the remote device 110. At 416, the local device(s) transmit data signal(s) as requested by the LHCP 104 to the remote device 110 via the data communication network. In one embodiment, the processing device 208 processes the data signals such that they are included in the web page along with the video signal from the imaging device 120 which is accessed by the remote device 110 via the data communication network.

At 418, the controller 118 receives audio signals generated by the RHCP 108. In one embodiment, the RHCP 108 has an audio device 204 which generates the audio signals from information verbalized by the RHCP 108 and transmits the audio signals to the controller 118 via the data communication network. The controller 118 sends the audio signals to the audio device 204. At 420, the audio device 204 generates a sound pattern from the received audio signals representative of the audio signals verbalized by the RHCP 108. Thus, the bidirectional transmission of audio signals via the data communication network, controller 118, and audio controller 118 allows the LHCP 104 and the RHCP 108 to verbally communicate remotely.

Also at 418, the local device(s) receive control signals for controlling a function performed by the local device(s). In one embodiment, a control form is used to associate inputs by the RHCP 108 to the remote device 110 with control signals. In another one embodiment, the control form is processed by the processing device 208 and accessed by the remote device 110 via the web page (or other web page included in the web site) and the data communication network. In yet another embodiment, the processing device 208 includes a modified control form in the web page for being accessed by the remote device 110 via the web page and the data communication network. At 422, the local device(s) perform the function associated with the control signal in response to receiving the control signal from the RHCP 108.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system comprising:
   a voice activated firewall which controls communication with devices located at a local health care facility;
   a local area network at the local health care facility, said local area network connected to the firewall and distributing signals to devices located at the local health care facility;
   a master controller located at the local health care facility and connected to the local area network for controlling the firewall;
   a plurality of local devices located at the local health care facility and connected to the local area network, each said local device comprising:
      a local controller for selectively receiving, as a function of a local user of the local device, local control data and remote control data, said local controller controlling the health care device in response to the local control data and the remote control data,
      a local health care device responsive exclusively to signals transmitted from the local controller, said signals being influenced by the selected control data received by the local controller,
      a local memory for storing a local control form for controlling a first set of features of the local health care device, said first local control form associated with the health care device located at the local health care facility and exclusively usable only by the particular local user, and
      a display and user interface for obtaining the local control data from the local user of the local device for controlling the local device, wherein said display displays the first local control form and the user interface obtains user input from the local user, wherein the first local control form generates the local control data as a function of the user input from the local user;
   an audio device at the local health care facility for obtaining a voice permission signal from the local user and for controlling the firewall via the master controller based on said voice permission signal, wherein said voice permission signal is a verbal instruction from the local user to authorize the firewall to permit a remote user to communicate and control at least one of the local devices via the local area network; and
   a remote device in communication with the local area network, said remote device having a display and user interface for obtaining remote control data for controlling one of the local device from the remote user of the remote device, wherein said display displays a second remote control form for controlling a second set of features of the local health care device and said user interface obtains user input from the remote user, wherein the second remote control form generates the remote control data as a function of the user input from the remote user; and
   wherein the second set of features of the local health care device controlled via the second remote control form differ from the first set of features of the local health care device controlled via the first local control form;
   wherein said remote device controls said one local device as permitted by said voice permission signal using said remote control data, said remote control data communicated via the local area network to the local controller of the one local device; and
   wherein the audio device receives a signal from the master controller and generates an audio signal as a function thereof for the local user, said received signal transmitted from the remote device via the local area network to the master controller; and
   wherein the master controller controls the firewall to restrict the remote control data communicated via the local area network and the second control form is based on said restrictions and based on said voice permission signal from the local user.

2. The system of claim 1 wherein the identity associated with the user of the remote device is indicative of an access level for controlling the local device and the second control form is based on said access level associated with the user.

3. The system of claim 1 wherein the second set of features of the local health care device are based on an identity of the remote user, and said identity has preferences associated therewith and the second control form is based on said user preferences.

4. The system of claim 1 wherein the second control form has at least one standardized feature associated with a function performed by the local health care device of the local device, said standardized feature appearing substantially similar in a plurality of control forms wherein said function is performed by a plurality of devices associated with the plurality of control forms.

5. The system of claim 1, further comprising:
   a processing server coupled to the plurality of remote devices and the local area network, said processing server receiving data from the master controller via the local area network, said received data indicating the one or more local devices selected by the master controller via the voice permission signal for linking to a remote device, said processing server locating said remote device based on the received data.

6. The system of claim 5 wherein the received data identifies a specific remote device and the processing server locates said specific remote device.

7. The system of claim 5 wherein the received data identifies one or more medical credentials of a user of a remote device and the processing server locates a particular remote device as a function of said identified medical credentials and as a function of users available to operate the plurality of remote devices.

8. The system of claim 5 wherein the received data includes a first collection of data for requesting communication with a remote device, and a second collection of data requested by the processing server after receiving said first data collection, said second collection of data identifying a particular remote device.

9. The system of claim 1 wherein the local health care device comprises at least one of the following: CT or MRI scanner, a hospital image retrieval system, hospital electronic health records (EHR), a digital stethoscope, an ultrasound device, a device for monitoring patient vital signs, a microscope, a bipolar coagulator, a camera, or a device instrumental in administering health care.

* * * * *